United States Patent
Esses

(10) Patent No.: US 9,522,208 B2
(45) Date of Patent: Dec. 20, 2016

(54) AIR FRESHENER

(71) Applicant: Alfred Esses, Brooklyn, NY (US)

(72) Inventor: Alfred Esses, Brooklyn, NY (US)

(73) Assignee: Alfred Esses, Brooklyn, NY (US)

( * ) Notice: Subject to any disclaimer, the term of this patent is extended or adjusted under 35 U.S.C. 154(b) by 0 days.

(21) Appl. No.: 14/641,049

(22) Filed: Mar. 6, 2015

(65) Prior Publication Data

US 2016/0022857 A1 Jan. 28, 2016

Related U.S. Application Data

(63) Continuation-in-part of application No. 14/341,382, filed on Jul. 25, 2014, now Pat. No. 9,408,936.

(51) Int. Cl.
| | |
|---|---|
| *A61L 9/00* | (2006.01) |
| *A62B 7/08* | (2006.01) |
| *A01G 13/06* | (2006.01) |
| *A61L 9/03* | (2006.01) |
| *B60H 3/00* | (2006.01) |

(52) U.S. Cl.
CPC ............. *A61L 9/032* (2013.01); *A61L 9/03* (2013.01); *B60H 3/0007* (2013.01)

(58) Field of Classification Search
CPC .............. A61L 9/00; A61L 9/03; A61L 9/037
USPC ........ 422/1, 5, 123, 125, 206; 392/386, 391, 392/394
See application file for complete search history.

(56) References Cited

U.S. PATENT DOCUMENTS

| | | | |
|---|---|---|---|
| 3,872,280 A * | 3/1975 | Van Dalen | A61L 9/03 128/203.27 |
| 6,099,137 A | 8/2000 | McCormack | |
| 6,102,660 A | 8/2000 | Lee | |
| 6,932,331 B1 | 8/2005 | Fan | |
| 7,687,037 B2 | 3/2010 | Wheatley et al. | |
| 7,687,038 B2 | 3/2010 | Wheatley et al. | |
| 8,480,960 B2 | 7/2013 | Wheatley et al. | |
| 8,662,480 B1 | 3/2014 | Irvin | |
| 8,673,223 B1 | 3/2014 | Finlay | |
| 2013/0164178 A1 | 6/2013 | Carmichael | |
| 2013/0266486 A1 | 10/2013 | Wu | |
| 2014/0112649 A1 | 4/2014 | Irvin et al. | |

(Continued)

FOREIGN PATENT DOCUMENTS

| | | |
|---|---|---|
| CN | 200947724 Y | 9/2007 |
| CN | 202641316 U | 1/2013 |

(Continued)

*Primary Examiner* — Monzer R Chorbaji
(74) *Attorney, Agent, or Firm* — Moritt Hock & Hamroff LLP; Steven S. Rubin, Esq.

(57) ABSTRACT

Technologies are generally described for systems, devices, and methods effective to disperse fragrance from a material. A material may be infused with a fragrance around a charging column of a collar. The collar may be positioned between a base and a cap. An insertion section may include electrodes effective to receive and conduct an electric current from an electric source. The base may include a fan mounted to the base. The cap may be attached to the collar. The cap may have a ring shaped cross section and may be effective to secure the material infused with the fragrance to the collar. Electric current may be received from the electrodes and may be effective to operate the fan. The fan may be effective to blow air through a first vent in the collar to disperse the fragrance from the material through a second vent in the cap.

20 Claims, 6 Drawing Sheets

(56) References Cited

U.S. PATENT DOCUMENTS

2014/0124594 A1    5/2014   Hsiao
2014/0158789 A1    6/2014   Haymond
2014/0161672 A1    6/2014   Wheatley et al.

FOREIGN PATENT DOCUMENTS

| CN | 202950996 U | 5/2013 |
|----|---|---|
| DE | 202004002799 U | 6/2004 |
| EP | 2977065 A1 | 1/2016 |
| GB | 2062199 A | 5/1981 |
| GB | 2292271 A | 2/1996 |
| KR | 20120125933 A | 11/2012 |

\* cited by examiner

AIR FRESHENER

CROSS REFERENCE TO RELATED APPLICATIONS

This application is a continuation-in-part of application Ser. No. 14/341,382 filed on Jul. 25, 2014, the entirety of which is incorporated herein by reference.

BACKGROUND

Air fresheners reduce or mask undesired odors and emit pleasant odors. Air fresheners typically emit a pleasant odor in the form of a fragrance. Air fresheners include sprays, candles, oils, gels, and plug-ins.

SUMMARY OF THE INVENTION

In one example, devices are generally described. In some examples, the devices may include an insertion section. In some examples, the insertion section may include a first side and a second side. In some other examples, the devices may further include electrodes. In various examples, the electrodes may be effective to receive and conduct an electric current and may be further effective to secure the device to an electric source. In various examples, the devices may further include a base. In some examples, a first end of the base may be attached to the insertion section. In some examples, the devices may further include a fan. In some examples, the fan may be mounted to the base. In some further examples, the fan may be electrically coupled to the electrodes. In some examples, the devices may further include a collar including a charging column and a vent. In various examples, the charging column may include a port. In various other examples, a second end of the base may be effective to attach to a first end of the collar. In some examples, the port may be electrically coupled to the electrodes. In some other examples, the vent may be effective to allow air blown by the fan to pass through the collar. In some further examples, the collar may be sized and shaped so as to hold a ring shaped material infused with a fragrance. In various examples, the devices may further include a cap. In some examples, the cap may have a ring shaped cross-section. In various examples, the cap may be sized and shaped so as to be connectable to the collar around a second end of the collar such that the port of the charging column may be accessible when the cap is connected to the collar.

In another example, devices are generally described. In some examples, the devices may include an insertion section. In some examples, the insertion section may include a first side and a second side. In some further examples, the devices may include electrodes. In some examples, the electrodes may be effective to receive and conduct an electric current. In some examples, the devices may further include a base. The base may be sized and shaped so as to fit securely within a cup holder. In some other examples, the base may be attached to the insertion section by a wire. In further examples, the devices may further include a collar including a charging column and a heating column. In various examples, the charging column may include a port. In some examples, the base may be effective to attach to a first end of the collar. In some other examples, the port may be electrically coupled to the electrodes. In various further examples, the heating column may be effective to provide heat to a ring shaped material infused with a fragrance. In some examples, the collar may be sized and shaped so as to hold the ring shaped material. In various examples, the devices may further include a cap. In some examples, the cap may have a ring shaped cross-section. The cap may be sized and shaped so as to be connectable to the collar around a second end of the collar such that the port of the charging column may be accessible when the cap is connected to the collar.

In another example, methods to disperse fragrance from a material are generally described. In some examples, the methods may include placing a material infused with a fragrance around a charging column of a collar. In some examples, the collar may be positioned between a first end of a base and a cap. In some further examples, a second end of the base may be attached to an insertion section. In various examples, the insertion section may include electrodes effective to receive and conduct an electric current from an electric source. In various further examples, the base may include a fan mounted to the base. In some examples, the fan may be electrically coupled to the electrodes. In some examples, the methods may further include attaching the cap to the collar. In some examples, the cap may have a ring shaped cross section and may be effective to secure the material infused with the fragrance to the collar. In some other examples, the methods may further include attaching the electrodes to the electric source. In some examples, the methods may further include receiving the electric current from the electrodes at the fan effective to operate the fan. In various examples, the fan may be effective to blow air through a first vent in the collar to disperse the fragrance from the material through a second vent in the cap.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims taken in conjunction with the accompanying drawings. Understanding that these drawings depict only some embodiments in accordance with the disclosure and are therefore not to be considered limiting of its scope, the disclosure will be described with additional specificity and detail by reference to the accompanying drawings in which:

Figure 1:
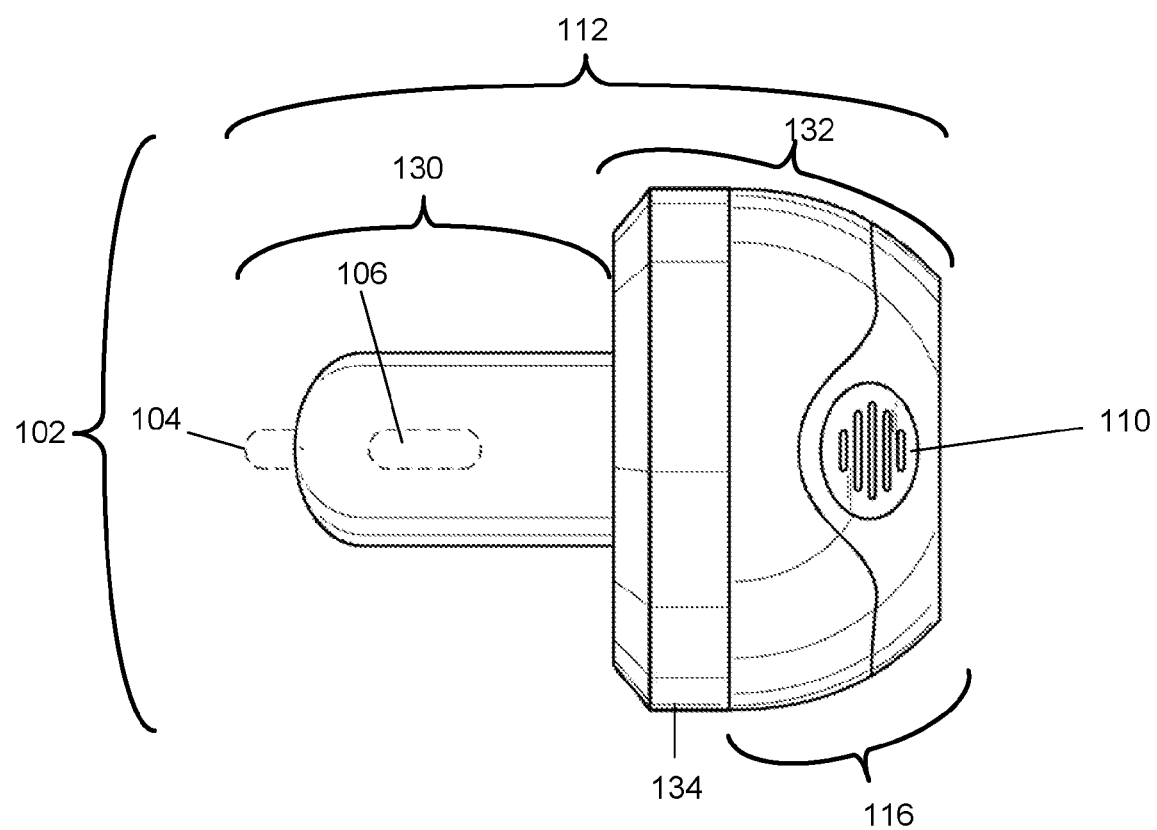
FIG. 1 is a side view of an air freshener.

all in accordance with an embodiment of the invention.

DETAILED DESCRIPTION

In the following detailed description, reference is made to the accompanying drawings which form a part thereof. In the drawings, similar symbols typically identify similar components unless context indicates otherwise. The illustrative embodiments described in the detailed description, drawings and claims are not meant to be limiting. Other embodiments may be utilized and other changes may be made without departing from the spirit or scope of the subject matter presented herein. It will be readily understood that the aspects of the present disclosure as generally described herein and as illustrated in the accompanying figures can be arranged, substituted, combined, separated and/or designed in a wide variety of different configurations all of which are explicitly contemplated herein.

FIG. 1 is a side view of an air freshener in accordance with an embodiment of the invention. An air freshener 102 may include a body 112 comprising an insertion section 130 connected to an outer section 132. Insertion section 130 of body 112 may have a cylindrical shape and may have a first and a second end. Insertion section 130 may include an anode electrode 104 extending axially from the first end. The second end of insertion section 130 may be connected to outer section 132. Insertion section 130 may include cathode electrodes 106 extending radially from the sides of insertion section 130. Insertion section 130 including anode electrode 104 and cathode electrodes 106, may be arranged such that air freshener 102 may be plugged into a cigarette lighter socket, such as a vehicle cigarette lighter socket, with the anode electrode 104 and the cathode electrodes 106 aligning and connecting to the electrodes of the vehicle cigarette lighter socket respectively. The current provided by the vehicle cigarette lighter socket may be direct current and may be 12 volts.

Outer section 132 may be substantially hemispherical shaped and include a cap 116 and a base 134. Outer section 132 may be connected to insertion section 130 axially at base 134. Base 134 may be substantially cylindrically shaped with a substantially larger radius than insertion section 130. Base 134 may have a first and a second side and may include flat edges, textured edges or be smooth. Base 134 may slightly taper in radius axially on the first side of base 134. The first side of base 134 may be attached to the second side of insertion section 130. Cap 116 may extend axially from base 134 on the second side of base 134. Cap 116 may be substantially hemispherical in shape and may be smooth and taper in radius along an axial direction away from base 134. Cap 116 may have a ring shaped cross-section defining an opening in the middle of cap 116 where the second end of base 134 may be exposed when cap 116 is connected to base 134. Cap 116 may include vents 110. Vents 110 may be grilled, slotted, screened, or any other venting configuration capable of allowing air to flow between inside of cap 116 and outside of cap 116.

Figure 2:
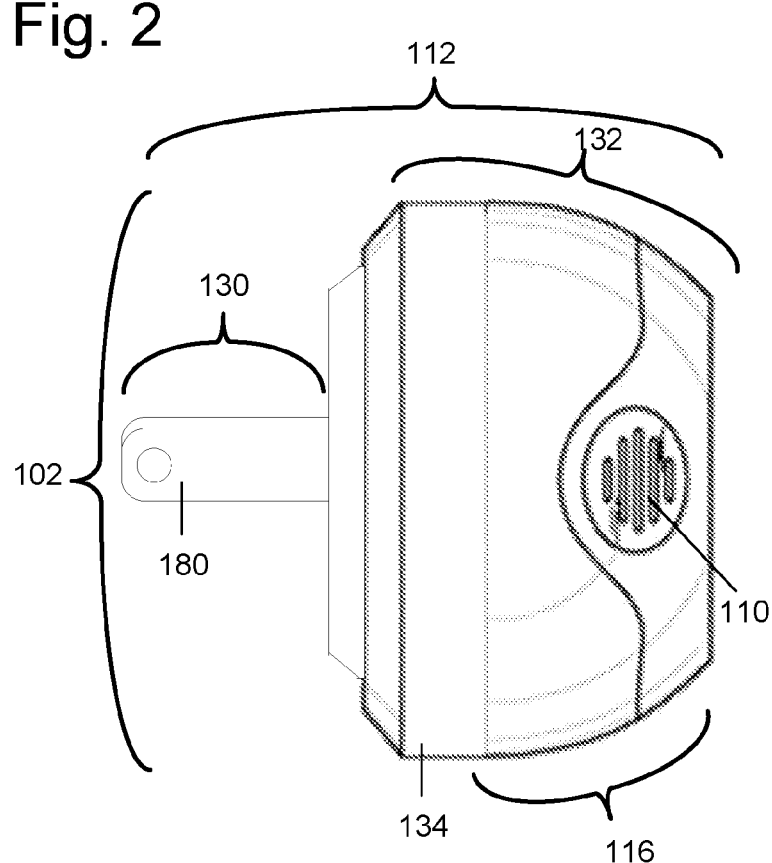
FIG. 2 is a side view of an air freshener with metal terminals.

FIG. 2 is a side view of air freshener 102 with metal terminals in accordance with an embodiment of the invention. Those components in FIG. 2 that are labeled identically to components of FIG. 1 will not be described again for the purposes of clarity. In another embodiment, insertion section 130 may include electrodes 140 that are metal prongs or terminals extending axially from base 134. Metal terminals 180 may be arranged such that air freshener 102 may be plugged into an electrical socket. Metal terminals 140 may secure air freshener 102 to an electric socket when plugged into the electric socket. An electrical current may be provided to metal terminals 180 and subsequently to air freshener 102 when metal terminals 180 are plugged into an electrical socket.

Figure 3:
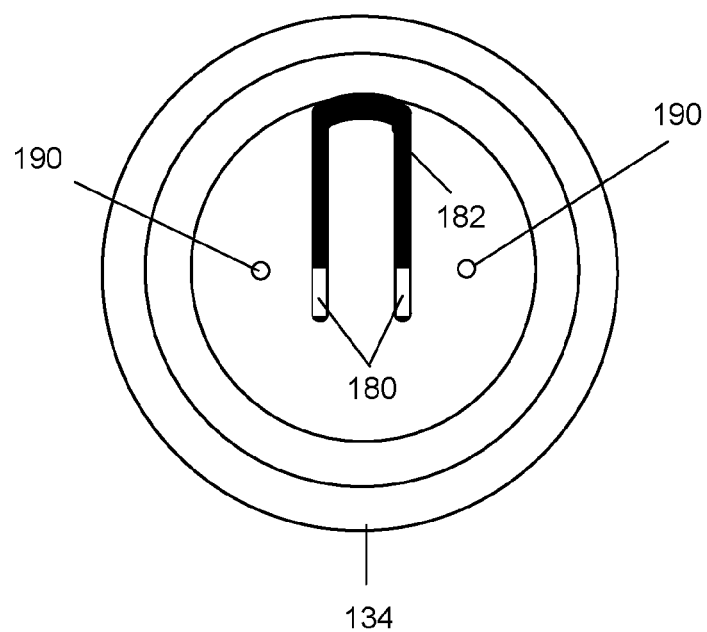
FIG. 3 is a rear view of an air freshener with metal terminals.

FIG. 3 is a rear view of air freshener 102 with metal terminals in accordance with an embodiment of the invention. Those components in FIG. 3 that are labeled identically to components of FIG. 1-2 will not be described again for the purpose of clarity. Metal terminals 180 in insertion section 130 may be retractable. Metal terminals 180 may be able to fold 90 degrees to range from perpendicular to the surface of the first side of base 134 to parallel to the surface of the first side of base 134. Grooves 182 may be present in the surface of base 134 such that metal terminals 140, when folded parallel to the surface of the first side of base 134, may recess into the surface of the first side of base 134. When recessed into the surface of the first side of base 134, metal terminals 140 may be completely submerged within the first side of base 134. Base 134 may sized and shaped so as to include one or more air intakes 190. Air intakes 190 may be effective to allow air to pass into and/or out of base 134. In some examples, air intakes 190 may be small holes, vents, slits or other openings in base 134 effective to allow air to pass into and out of base 134. In some examples, air intakes 190 may be located on the first side of base 134.

Figure 4:
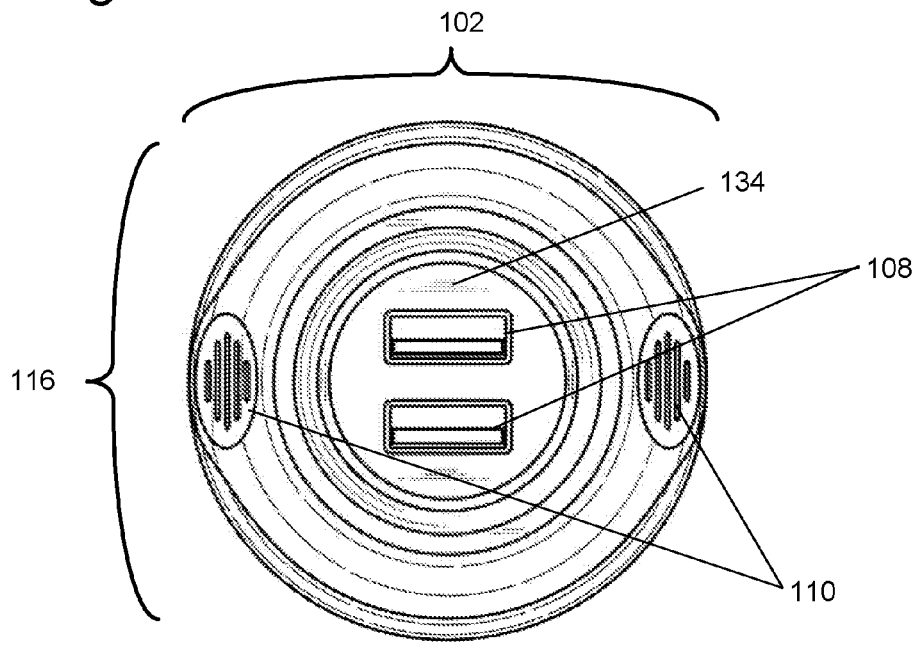
FIG. 4 is a front view illustrating two ports of an air freshener.

FIG. 4 is a front view illustrating two ports of air freshener 102 in accordance with an embodiment of the invention. Those components in FIG. 4 that are labeled identically to components of FIG. 1-3 will not be described again for the purposes of clarity. Air freshener 102 may include ports 108 and grilled vents 110. Ports 108 may be included in the second side of base 134 and grilled vents 110 may be included in cap 116. Ports 108 may be universal serial bus (USB) ports and may be accessible when cap 116 is attached to base 134. Cap 116 may have a ring shaped cross-section and may be sized and shaped so as to be connectable to base 134 around the second end of base 134 such that ports 108 are accessible when cap 116 is connected. Ports 108 may be electrically coupled to anode electrode 104 and cathode electrode 106. In some examples, ports 108 may be powered by an electric current from anode electrode 104 and cathode electrode 106 (illustrated in FIG. 1) when connected to vehicle cigarette lighter socket electrodes. In another example, ports may be powered by an electric current from metal terminals 140 (illustrated in FIG. 2-3) when plugged into an electric socket. As described in more detail below, vents 110 in cap 116 may allow fragrance to flow from air freshener 102.

Figure 5:
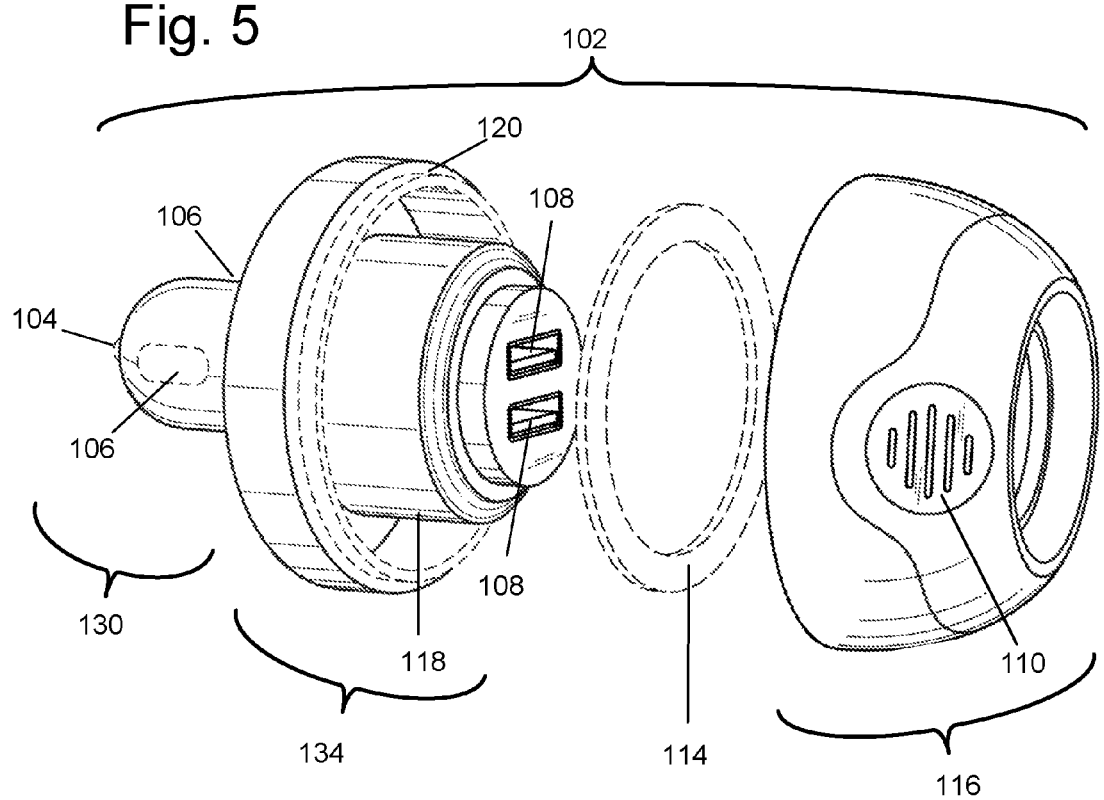
FIG. 5 is an angled side perspective view illustrating a body, a disk, and a cap enclosure of an air freshener.

FIG. 5 is an angled side perspective view illustrating a body, a disk, and a cap enclosure of car air freshener 102 in accordance with an embodiment of the invention. Those components in FIG. 5 that are labeled identically to components of FIGS. 1-4 will not be described again for the purposes of clarity. Air freshener 102 may include insertion section 130, base 134, a disk 114 and cap 116. Insertion section 130 may include anode electrode 104 and cathode electrodes 106, and may be attached to base 134. Base 134 may include USB ports 108, and collar 118. Current provided by a vehicle cigarette lighter socket may travel from electrode cathode 106 to electrode anode 104 and provide power to USB ports 108.

Disk 114 may be a liquid oil, gel or solid material infused with a fragrance. Fragrances may be any desirable fragrance including fruit scents, new car smell, etc. Disk 114 may be in the shape of a flat ring and may fit around collar 118. In some examples, collar 118 may be heated when a current provided by vehicle cigarette lighter socket travels from electrode cathode 106 to electrode anode 104. Heating of collar 118 by electric current provided by vehicle cigarette lighter socket may release fragrance from disk 114.

Cap 116 may secure disk 114 to collar 118 and base 134 when cap 116 is attached to base 134. Cap 116 may attach to base 134 and be secured to base 134 by locking mechanism 120. In some examples, locking mechanism 120 may include protrusions on base 134 onto which cap 116 may snap. In some other examples, locking mechanism 120 may include threads which may be effective to screw cap 116 onto base 134. Fragrance emitted from heating of disk 114 may disperse through vents 110 in cap 116 to freshen air proximate to air freshener 102.

For example, insertion section 130 may be placed into a vehicle cigarette lighter socket such that anode electrode 104 and cathode electrodes 106 align with electrodes in vehicle cigarette lighter socket. Electric current may travel from vehicle cigarette lighter socket to cathode electrodes 106 through air freshener 102 circuitry to anode electrode 104 and back to vehicle cigarette lighter socket. Electric current may be direct current and may be 12 volts. Air freshener 102 circuitry may be configured to supply electric current to USB ports 108. USB ports 108 may function to supply power to connected USB cables for powering and/or charging devices attached to a connected USB cable. Air freshener 102 circuitry may further be configured to provide electric current to heat collar 118 in base 134. Collar 118 may be heated by electric current as current travels from cathode electrodes 106 to anode electrode 104. Collar 118, heated by electric current, may conduct heat to disk 114 located and secured around collar 118 by cap 116. Heating of disk 114 may release fragrance infused within material of disk 114. Released fragrance may diffuse into the air. Air with diffused fragrance may disperse through vents 110 and provide fragrance to air proximate to air freshener 102.

Figure 6:
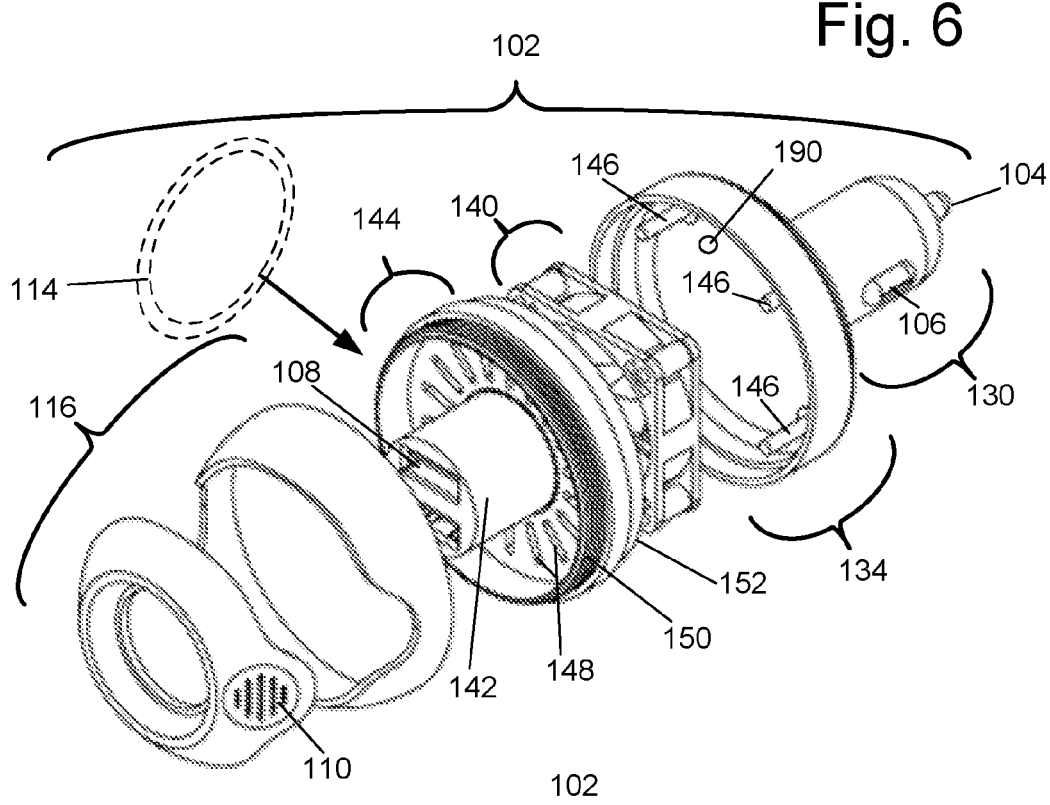
FIG. 6 is an angled side perspective view illustrating an air freshener including a fan and vented collar.
Figure 7:
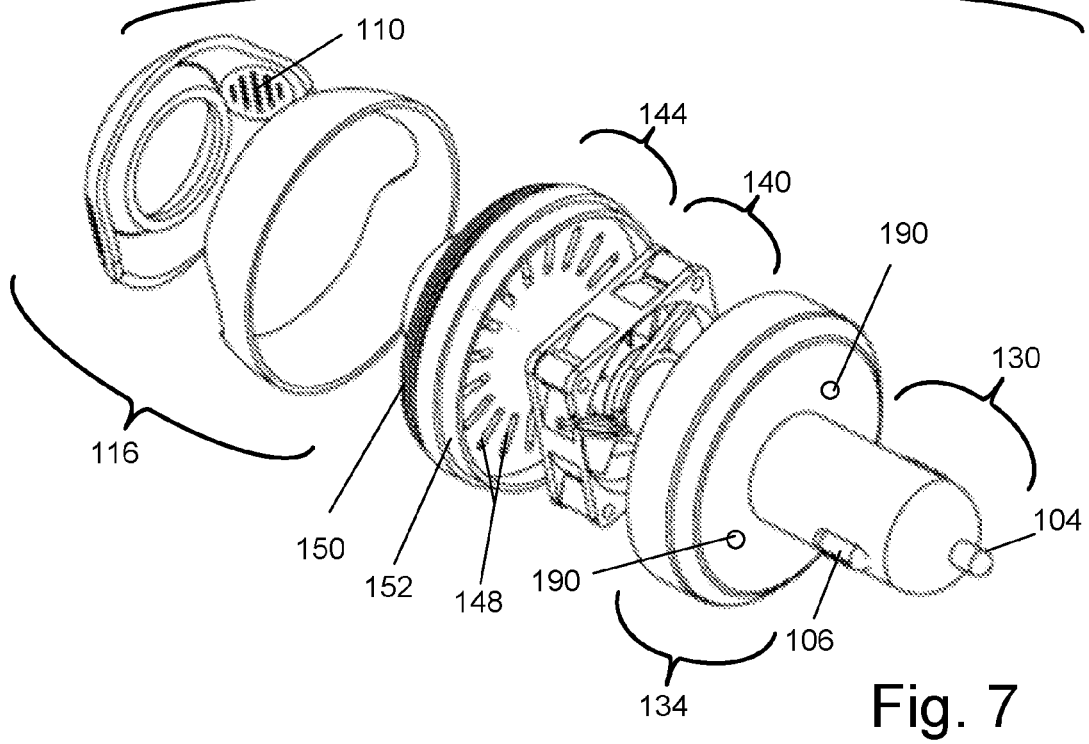
FIG. 7 is another angled side perspective view illustrating an air freshener including a fan and vented collar.

FIGS. 6 and 7 illustrate angled side perspective views of an air freshener including a fan 140 and a vented collar 144 in accordance with an embodiment of the invention. Those components in FIGS. 6 and 7 that are labelled identically to components of FIGS. 1-5 will not be described again for the purposes of clarity. In some examples, air freshener 102 may include fan 140, vented collar 144, and charging column 142. In various examples, fan 140 may be mounted within base 134. Fan 140 may include a motor and one or more blades and may be effective to blow air through vents 148 of vented collar 144. Fan 140 may be electrically coupled to anode electrode 104 and cathode electrode 106. For example, current provided from a power source such as an electrical outlet or vehicle cigarette lighter, may travel from electrode cathode 106 to electrode anode 104 and provide power to fan 140. In various examples, fan 140 may be turned on and/or off using a button, switch, or other mechanism on air freshener 102. Vented collar 144 may include charging column 142. Vented collar 144 may include a first end and a second end. The first end of vented collar 144 may attach to base 134. The second end of vented collar 144 may be effective to attach to cap 116.

Charging column 142 may include USB ports 108. In some examples, collar 118 of FIG. 5 may be formed around charging column 142 such that heat may be provided to disk 114. Disk 114 may be configured to fit around charging column 142 and/or collar 118. Disk 114 may be positioned to rest on top of vents 148 of vented collar 144. Fan 140 may be effective to blow air through vents 148. Air intakes 190 may allow air to be pulled into air freshener 102 while fan 140 is in operation. The air blown through vents 148 by fan 140 may be effective to mix with fragrance released from disk 114 to produce fragrant air. Fragrant air may be blown by fan 140 through vents 110 in cap 116 to freshen air proximate to air freshener 102.

In some examples, vented collar 144 may attach to cap 116 and be secured to cap 116 by locking mechanism 150. Locking mechanism 150 may secure cap 116 to vented collar 144. In some examples, locking mechanism 150 may include protrusions on vented collar 144 onto which cap 116 may snap. In some other examples, locking mechanism 150 may include threads which may be effective to screw cap 116 onto vented collar 144. Similarly, vented collar may be secured to base 134 by a locking mechanism 152. Locking mechanism 152 may include threads and/or protrusions effective to attach vented collar 144 to base 134. In various examples, fan 140 may be mounted to base 134 using mounting structures 146. In some examples, mounting structures 146 may include molded mounting rods, screws or other structures effective to secure base 134 to fan 140.

Figure 8:
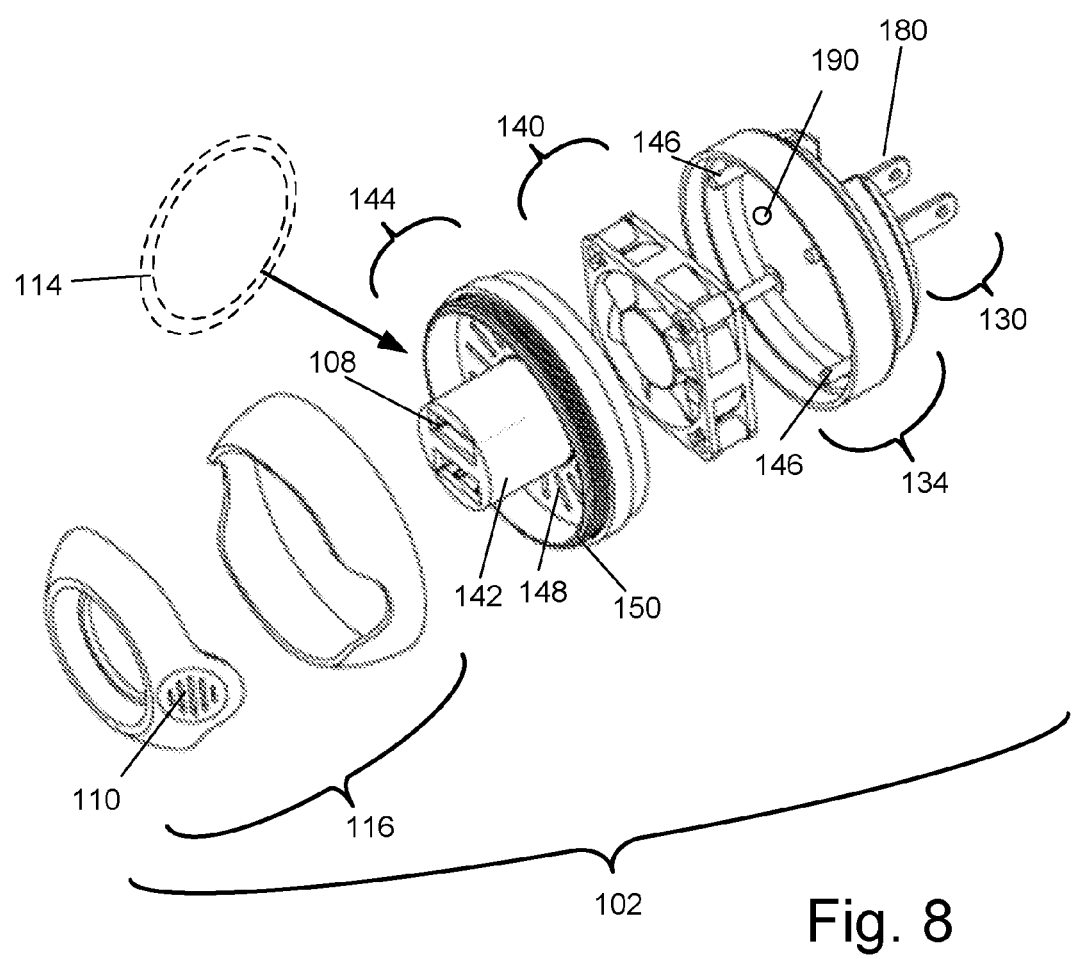
FIG. 8 is an angled side perspective view illustrating an air freshener including a fan, a vented collar, and metal terminals.

FIG. 8 is an angled side view of air freshener 102 with metal terminals in accordance with an embodiment of the invention. Those components in FIG. 8 that are labelled identically to components of FIGS. 1-7 will not be described again for purposes of clarity. In some examples, air freshener 102 may include vented collar 144 and fan 140 in an embodiment with metal terminals 180, so that air freshener 102 may be plugged into an electrical outlet. In some examples, insertion section 130 may include metal terminals 180. Metal terminals 180 may include, for example, electrodes and/or prongs which may extend axially from base 134.

Figure 9:
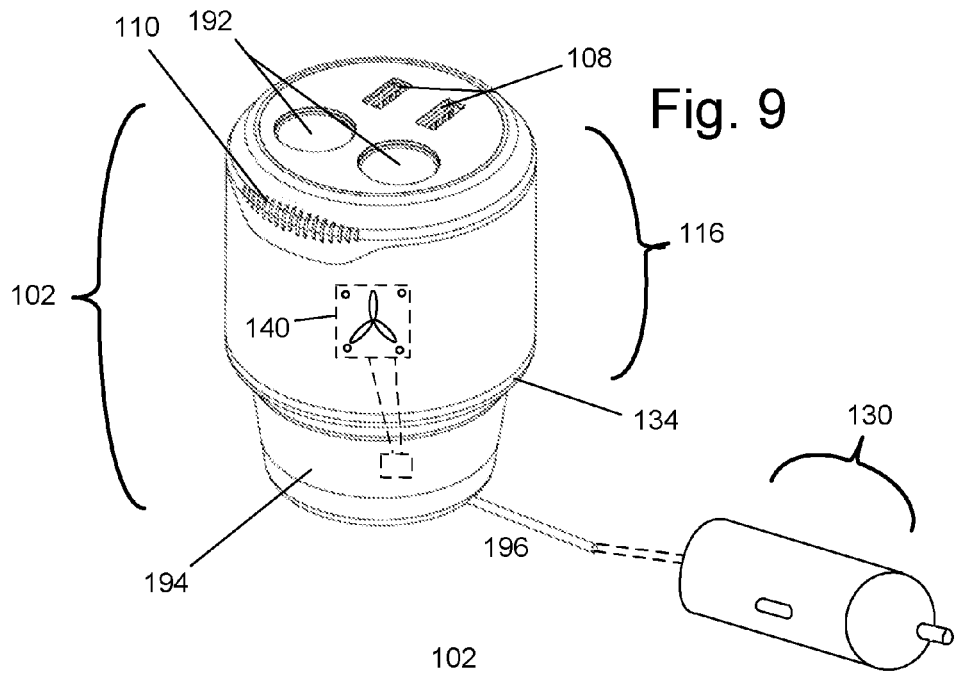
FIG. 9 illustrates a front view of an air freshener arranged so as to fit in a cup holder.

FIG. 9 illustrates a front view of air freshener 102 sized, shaped, and arranged so as to fit in a cup holder. Air freshener 102 may include cap 116. Cap 116 may include vents 110. In some examples, air freshener 102 may include ports 192. In some examples, ports 192 may be effective to provide direct current from anode electrode 104 and/or cathode electrode 106. The direct current may be at 12 volts. In various examples, air freshener 102 may include a portion 194. Portion 194 may be sized and shaped in such a way as to fit securely within a cup holder. In various examples, portion 194 may be attached to a base 134 or may be part of base 134. In embodiments of air freshener 102 which include portion 194, a wire 196 may attach insertion section 130 to portion 194 and/or base 134. Wire 196 may be electrically coupled to ports 108 and/or ports 192. Wire 196 may be effective to conduct direct current from a power source to ports 108, 192 and/or fan 140. In some examples, fan 140 may be disposed inside portion 194, or within cap 116, as denoted by dashed lines.

Figure 10:
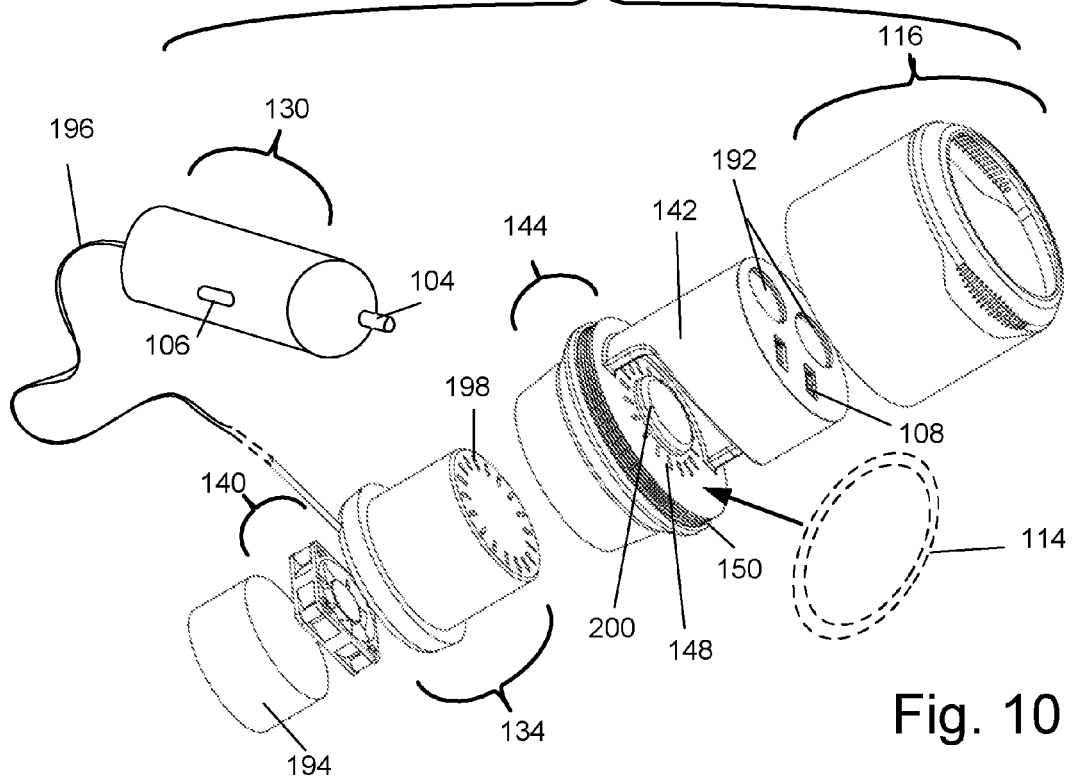
FIG. 10 is an angled side perspective view illustrating an air freshener arranged so as to fit in a cup holder.

FIG. 10 is an angled side perspective view of air freshener 102 arranged so as to fit in a cup holder. In some examples, fan 140 may be secured to portion 194. In other examples, fan 140 may be secured inside base 134. In various examples, base 134 may include vents 198. Vents 198 may allow air blown from fan 140 to travel from base 134 to vented collar 144. In various examples, disk 114 may be placed on vents 148 of vented collar 144 such that air traveling through vented collar may interact with disk 114. In some examples, vented collar 144 may further include heating column 200. Heating column 200 may be effective to provide heat to disk 114. For example, heating column 200 may be heated by a heating element disposed within heating column 200. The heating element may be coupled to, and receive electric current from, anode electrode 104 and/or cathode electrode 106. Disk 114 may fit around heating column 200. In various examples, fan 140, ports 108, heating column 200, and/or ports 192 may be electrically coupled to anode electrode 104 and cathode electrode 106. In some examples, fan 140, ports 108, heating column 200, and/or ports 192 may be powered by an electric current from anode electrode 104 and/or cathode electrode 106 when connected to vehicle cigarette lighter socket electrodes.

Among other potential benefits, a device in accordance with the disclosure may provide a desired fragrance within a vehicle while also providing operational USB ports for use. Vehicles with a single cigarette lighter socket may be able to utilize the single socket for more than one purpose. Multiple devices, such as global positioning devices (GPS), cell phone chargers, media players, etc., may be attached to the USB ports while freshening the air of the vehicle. A fan disposed inside the air freshener below the vented collar may aid in the dispersal of the fragrance from the air freshener. In some examples, air fresheners may be sized and shaped so as to fit securely into the cup holder of an automobile.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising:
   an insertion section, wherein the insertion section includes:
      a first side and a second side;
   electrodes wherein the electrodes are effective to receive and conduct an electric current and further effective to secure the device to an electric source;
   a base, a first end of the base attached to the insertion section;
   a fan, wherein the fan is mounted to the base, and wherein the fan is electrically coupled to the electrodes;
   a collar including a charging column and a vent, the charging column including a port, wherein:
      a second end of the base is effective to attach to a first end of the collar;
      the port is electrically coupled to the electrodes;
      the vent is effective to allow air blown by the fan to pass through the collar; and
      the collar is sized and shaped so as to hold a ring shaped material infused with a fragrance; and
   a cap, where the cap has a ring shaped cross-section and is sized and shaped so as to be connectable to the collar around a second end of the collar such that the port of the charging column is accessible when the cap is connected to the collar.

2. The device of claim 1, wherein the electrodes are configured to align and connect to electrodes of a vehicle cigarette lighter socket.

3. The device of claim 1, wherein the electrodes are configured to align and connect to electrodes in an electric outlet.

4. The device of claim 1, wherein the material infused with the fragrance includes a liquid oil, a gel, or a solid and the material is in the shape of a flat ring.

5. The device of claim 1, wherein the vent is a first vent, and wherein the cap includes a second vent effective to disperse the fragrance.

6. The device of claim 1, wherein the base is sized and shaped so as to fit securely into a cup holder, and wherein the first end of the base is attached to the insertion section by a wire.

7. The device of claim 1, wherein:
   the base includes threads on the second side of the base; and
   the collar is effective to be screwed onto the threads so that the collar is secured to the base.

8. The device of claim 1, wherein the base is sized and shaped so as to include an air intake on the first end of the base, wherein the air intake is effective to allow air to pass into or out of the base.

9. The device of claim 8, wherein:
   the collar includes threads on the second end of the collar; and
   the cap is effective to be screwed onto the threads so that the cap is secured to the collar.

10. A device comprising:
    an insertion section, wherein the insertion section includes:
       a first side and a second side;
    electrodes wherein the electrodes are effective to receive and conduct an electric current;
    a base, wherein the base is sized and shaped so as to fit securely within a cup holder, and wherein the base is attached to the insertion section by a wire;
    a collar including a charging column and a heating column, wherein the charging column includes a port, wherein:
       the base is effective to attach to a first end of the collar;
       the port is electrically coupled to the electrodes;
       the heating column is effective to provide heat to a ring shaped material infused with a fragrance; and
       the collar is sized and shaped so as to hold the ring shaped material; and
    a cap, where the cap has a ring shaped cross-section and is sized and shaped so as to be connectable to the collar around a second end of the collar such that the port of the charging column is accessible when the cap is connected to the collar.

11. The device of claim 10, wherein the electrodes are configured to align and connect to electrodes of a vehicle cigarette lighter socket.

12. The device of claim 10, wherein the electrodes are configured to align and connect to electrodes in an electric outlet.

13. The device of claim 10, wherein the material infused with the fragrance includes a liquid oil, a gel, or a solid and the material is in the shape of a flat ring.

14. The device of claim 10, wherein the cap includes a vent effective to disperse the fragrance.

15. The device of claim 10, further comprising attaching the cap to the first end of the collar with a locking mechanism, wherein the locking mechanism includes protrusions on the first end of the collar and the cap is effective to snap onto the protrusions.

16. The device of claim 10, further comprising attaching the cap to the first end of the collar with a locking mechanism, wherein the locking mechanism includes threads on the first end of the collar and the cap screws onto the threads to secure the cap to the collar.

17. The device of claim 10, further comprising a fan, wherein the fan is mounted to the base, and wherein the fan is electrically coupled to the electrodes.

18. The device of claim 17, wherein the collar includes a vent, wherein the vent is effective to allow air blown by the fan to pass through the collar.

19. The device of claim 10, wherein the material infused with the fragrance is ring shaped, and wherein the heating column is sized and shaped so as to hold the ring shaped material infused with the fragrance around the heating column.

20. A method to disperse fragrance from a material, the method comprising:
- placing a material infused with a fragrance around a charging column of a collar; the collar being positioned between a first end of a base and a cap, a second end of the base attached to an insertion section, the insertion section including electrodes effective to receive and conduct an electric current from an electric source, the base including a fan mounted to the base, the fan being electrically coupled to the electrodes;
- attaching the cap to the collar, the cap having a ring shaped cross section and effective to secure the material infused with the fragrance to the collar;
- attaching the electrodes to the electric source; and
- receiving the electric current from the electrodes at the fan effective to operate the fan, wherein the fan is effective to blow air through a first vent in the collar to disperse the fragrance from the material through a second vent in the cap.

* * * * *